(12) United States Patent
Fank et al.

(10) Patent No.: US 7,354,519 B1
(45) Date of Patent: Apr. 8, 2008

(54) METHOD AND APPARATUS FOR FABRICATING A STENT

(75) Inventors: Steven A. Fank, Darwin, MN (US); Kurt C. Swanson, Hutchinson, MN (US); Paul D. Borscheid, Hutchinson, MN (US); Kurt S. Kruckman, Glencoe, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 794 days.

(21) Appl. No.: 10/770,230

(22) Filed: Feb. 2, 2004

Related U.S. Application Data

(60) Provisional application No. 60/444,491, filed on Feb. 3, 2003.

(51) Int. Cl.
*B32B 1/08* (2006.01)

(52) U.S. Cl. .................... 216/8; 216/9; 216/41; 216/50

(58) Field of Classification Search .................... 216/8, 216/9, 41, 50
See application file for complete search history.

(56) References Cited

U.S. PATENT DOCUMENTS

| | | | |
|---|---|---|---|
| 4,496,216 A | 1/1985 | Cowan | |
| 4,595,957 A | 6/1986 | Holthusen | |
| 4,724,465 A | 2/1988 | Davies | |
| 5,292,625 A | 3/1994 | McFadden et al. | |
| 5,421,955 A | 6/1995 | Lau et al. | |
| 5,488,406 A | 1/1996 | Rubi | |
| 5,514,154 A | 5/1996 | Lau et al. | |
| 5,569,295 A | 10/1996 | Lam | |
| 5,728,158 A | 3/1998 | Lau et al. | |
| 5,741,429 A | 4/1998 | Donadio, III et al. | |
| 5,766,238 A | 6/1998 | Lau et al. | |
| 5,776,161 A | 7/1998 | Globerman | |
| 5,855,802 A | 1/1999 | Acciai et al. | |
| 5,902,475 A | 5/1999 | Trozera et al. | |
| 5,916,234 A | 6/1999 | Lam | |

(Continued)

FOREIGN PATENT DOCUMENTS

JP  5-185002  7/1993

(Continued)

*Primary Examiner*—Binh X. Tran
(74) *Attorney, Agent, or Firm*—Faegre & Benson LLP

(57) ABSTRACT

A method for fabricating a tubular article having a wall structure defined by a selected pattern. The method includes the steps of providing a tube having an outer surface and an inner surface; coating the outer surface with first photosensitive resist; exposing the selected pattern portions of the coated outer surface; developing the first photosensitive resist coated on the outer surface; coating the inner surface with second photosensitive resist; and exposing the tube to an etchant to form a tubular article having the wall structure defined by the selected pattern. The second photosensitive resist is more brittle than the first photosensitive resist when the first and second photosensitive resist are dry. An apparatus for exposing a photosensitive resist-coated tube to laser. The device includes an elongated tubular member having an aperture extending through its wall. The outside diameter of the elongated tubular member is smaller than the inside diameter of the tube, so that the elongated tubular member can be positioned inside the tube without touching the inner surface of the tube. The apparatus further includes a laser beam and a reflective member for transmitting the laser beam to selected pattern portions of the coated inner surface of the tube through the aperture of the elongated tubular member.

12 Claims, 11 Drawing Sheets

U.S. PATENT DOCUMENTS

| | | |
|---|---|---|
| 6,027,863 A | 2/2000 | Donadio, III |
| 6,056,776 A | 5/2000 | Lau et al. |
| 6,066,168 A | 5/2000 | Lau et al. |
| 6,080,191 A | 6/2000 | Summers |
| 6,090,127 A | 7/2000 | Globerman |
| 6,107,004 A | 8/2000 | Donadio, III |
| 2001/0013166 A1 | 8/2001 | Yan |
| 2002/0017503 A1 | 2/2002 | Banas et al. |
| 2002/0038767 A1 | 4/2002 | Trozera |
| 2004/0098101 A1 * | 5/2004 | Kuribayashi et al. ...... 623/1.15 |

FOREIGN PATENT DOCUMENTS

| | | |
|---|---|---|
| JP | 5-287490 | 11/1993 |

* cited by examiner

METHOD AND APPARATUS FOR FABRICATING A STENT

REFERENCE TO RELATED APPLICATION

This application claims the benefit of U.S. Provisional Application No. 60/444,491, filed Feb. 3, 2003, and entitled METHOD AND APPARATUS FOR FABRICATING A STENT, which is hereby incorporated by reference in its entirety.

FIELD OF THE INVENTION

The present invention relates generally to a method and apparatus for fabricating a tubular article having a wall structure defined by a selected pattern. More particularly, the invention is directed to an improved method and apparatus for fabricating a stent.

BACKGROUND OF THE INVENTION

Stents are generally cylindrically shaped prosthetic implants functioning to hold open and sometimes expand a segment of a blood vessel or other anatomical lumen. They are particularly suitable for supporting and preventing a torn or injured arterial lining from occluding a fluid passageway. Stents are typically formed of a cylindrical metal "mesh type" structure that can expand when pressure is internally applied. Alternatively, they can be formed of wire wrapped into a cylindrical shape.

Stents can be used in a variety of tubular structures in the body including, but not limited to, arteries and veins, ureters, common bile ducts, and the like. Stents are used to expand a vascular lumen or to maintain its patency after angioplasty or atherectomy procedures, overlie an aortic dissecting aneurysm, tack dissections to the vessel wall, eliminate the risk of occlusion caused by flaps resulting from the intimal tears associated with primary interventional procedure, or prevent elastic recoil of the vessel.

Stents may be utilized after atherectomy, which excises plaque, or cutting balloon angioplasty, which scores the arterial wall prior to dilatation, to maintain acute and long-term patency of the vessel. Stents may be utilized in by-pass grafts as well, to maintain vessel patency. Stents can also be used to reinforce collapsing structures in the respiratory, biliary, urological, and other tracts.

A stent fabrication method and apparatus is described in U.S. Pat. No. 5,855,802. This patent discloses a method for forming a tubular article having a perforated annular wall, which includes the steps of coating the exterior and interior cylindrical surfaces of a tubular member with photoresist, exposing selected portions of the photoresist coated surfaces to light, developing the coating, and then etching the coating to remove unexposed portions of the coating and immediate underlying portions of the annular wall to form a tubular article having a wall structure defined by a skeletal framework. This patent also discloses an apparatus for exposing the light sensitive coating disposed on the tubular member. The method and apparatus embodying this patent are particularly suitable for forming stents that support the walls of weak human arteries.

U.S. Pat. No. 5,902,475 describes a method of fabricating a stent by processing a tubular member. The method includes the steps of coating the outer surface of the tubular member with photosensitive resist, exposing a selected portion of the outer surface to a light source, immersing the tubular member in a resist developer, and then processing the treated tubular member by electrochemical etching process.

Stent fabrication methods and devices are also described, for example, in U.S. Pat. Nos. 5,421,995, 5,741,429, 5,766,238, 6,027,863, 6,056,776, and 6,107,004. There, however, remains a continuing need for improved apparatuses and methods for fabricating stents.

SUMMARY OF THE INVENTION

The present invention is directed to a method for fabricating a tubular article having a wall structure defined by a selected pattern. The method includes the steps of providing a tube having an outer surface and an inner surface; coating the outer surface of the tube with first photosensitive resist; exposing the selected pattern portions of the coated outer surface of the tube; developing the first photosensitive resist coated on the outer surface of the tube; coating the inner surface of the tube with second photosensitive resist; and exposing the tube to an etchant to form a tubular article having the wall structure defined by the selected pattern. The second photosensitive resist coated on the inner surface is more brittle than the first photosensitive resist coated on the outer surface when the first and second photosensitive resists are dry.

Another method for fabricating a tubular article having a wall structure defined by a selected pattern includes the steps of providing a tube having an outer surface and an inner surface; coating the outer and inner surfaces of the tube with photosensitive resist; exposing the selected pattern portions of the coated outer and inner surfaces of the tube; developing the photosensitive resist coated on the outer and inner surfaces of the tube; and exposing the tube to an etchant to form a tubular article having the wall structure defined by the selected pattern. The photosensitive resist coated on the outer and inner surfaces of the tube is relatively flexible and strong when it is dry.

The present invention is also directed to an apparatus for exposing a photosensitive resist-coated tube to laser. In one embodiment of the present invention, the apparatus also includes an elongated tubular member having a wall defined by its exterior and interior surfaces, as well as an aperture extending through the wall. The outside diameter of the elongated tubular member is smaller than the inside diameter of the tube, so that the elongated tubular member can be positioned inside the tube without touching the inner surface of the tube. The apparatus further includes a laser beam and a reflective member for transmitting the laser beam to selected pattern portions of the coated inner surface of the tube through the aperture of the elongated tubular member. The apparatus further includes a rotary drive motor for rotating the tube about its longitudinal axis and linear drive motor for moving the tube along its longitudinal axis.

In an alternative embodiment of the present invention, the apparatus includes an elongated tubular member having a wall defined by its exterior and interior surfaces, as well as an aperture extending through the wall. The outside diameter of the elongated tubular member is smaller than the inside diameter of the tube, so that the elongated tubular member can be positioned inside the tube without touching the inner surface of the tube. The apparatus additionally includes a first laser beam and a reflective member for transmitting the first laser beam to selected pattern portions of the coated inner surface of the tube through the aperture of the elongated tubular member. The apparatus also includes a second laser beam being transmitted to selected pattern portions of the coated outer surface of the tube. The apparatus further includes a rotary drive motor for rotating the tube about its longitudinal axis and linear drive motor for moving the tube along its longitudinal axis.

DETAILED DESCRIPTION OF THE INVENTION

Figure 1:
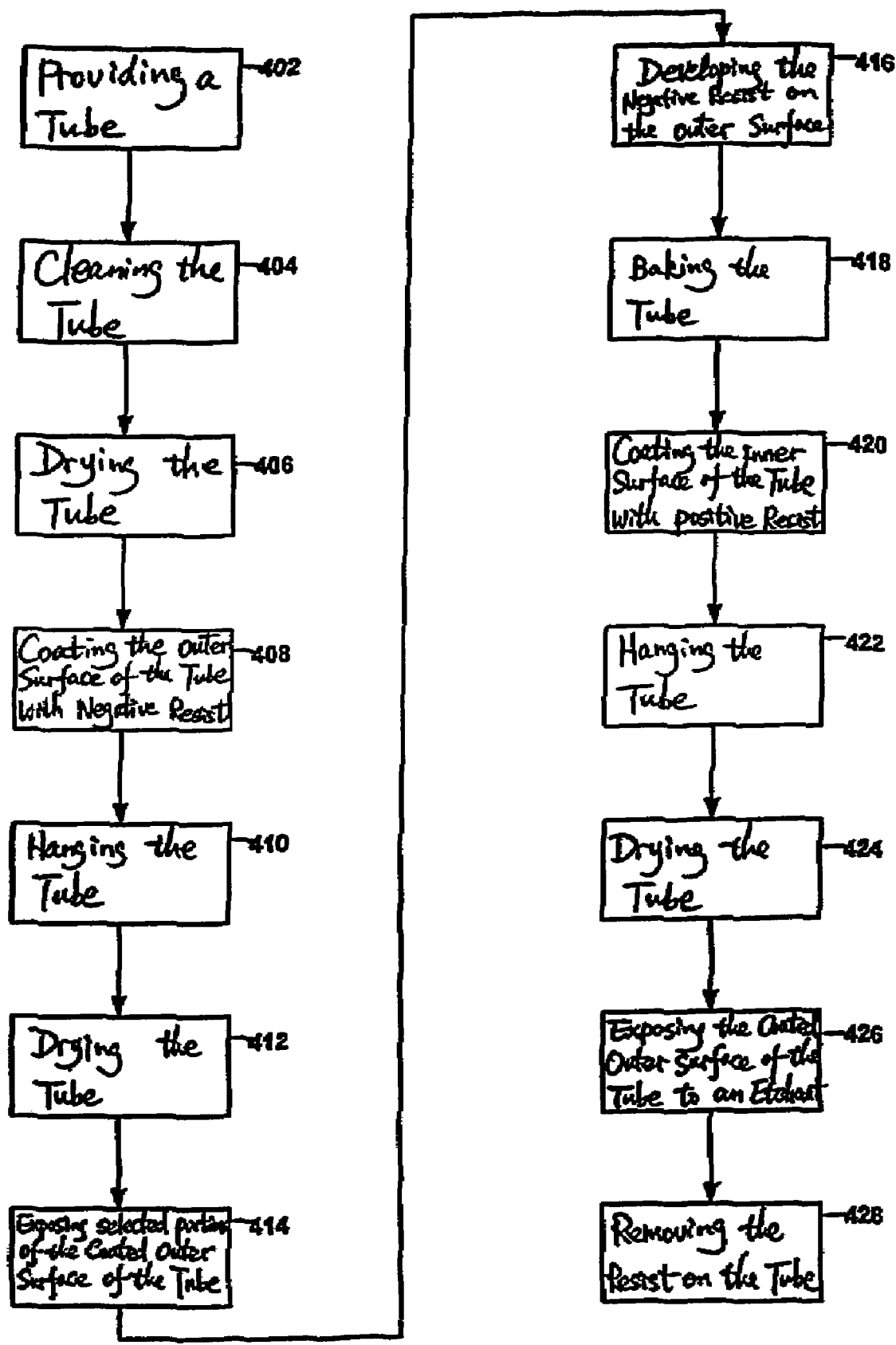
FIG. 1 is a flow chart illustrating the principal steps of the stent fabrication method using single side etching in accordance with the present invention.
Figure 2:
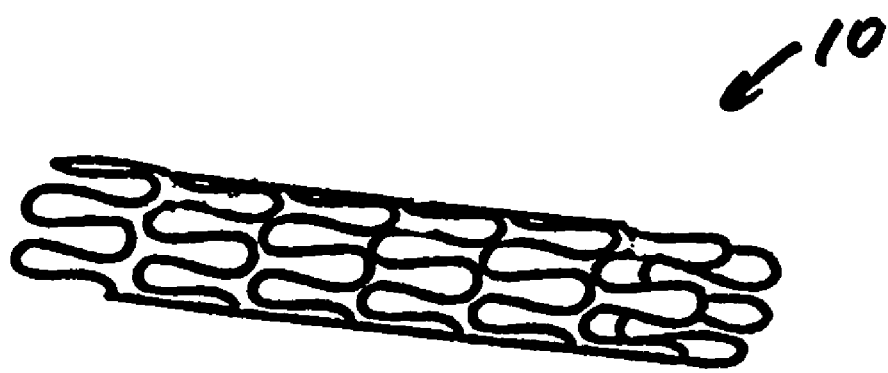
FIG. 2 is an isometric view of a stent manufactured in accordance with the method of the present invention.
Figure 3:
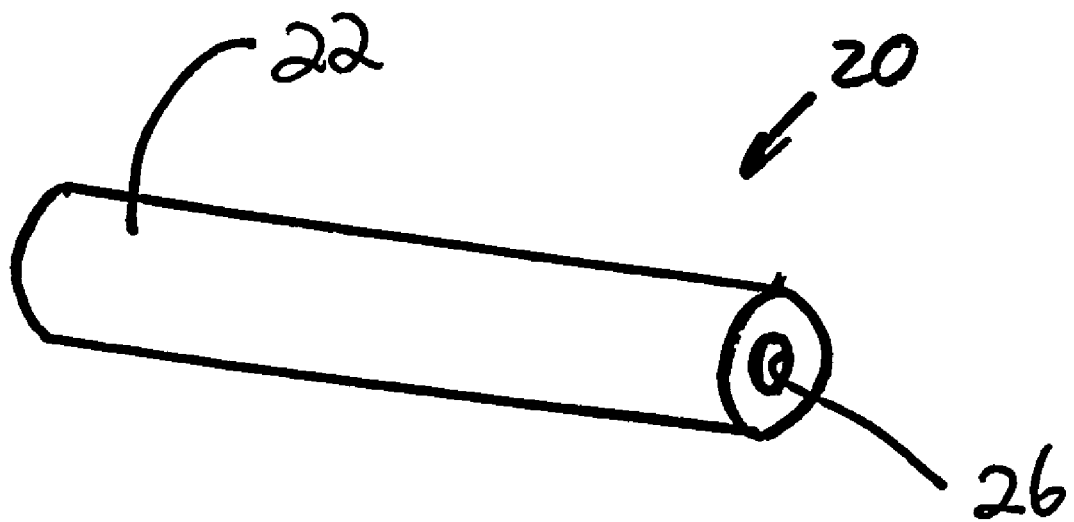
FIG. 3 is an isometric view of a tube processed for fabrication of the stent shown in FIG. 2.

FIG. 1 is a flow chart illustrating the principal steps of a method of fabricating a tubular article having a wall structure defined by a selected pattern using single side etching in accordance with the present invention. The tubular article, such as a radially expandable stent 10, is shown in FIG. 2. Referring to FIG. 3, the stent 10 is made by processing a tube 20 having a solid annular wall defined by an outer cylindrical surface 22 and an inner cylindrical surface 26. As indicated in block 402 of FIG. 1, the first step of fabricating a stent is providing the tube 20. The tube 20 is preferably formed of titanium, tantalum, stainless steel, platinum, gold alloy or gold/platinum alloy, a polymeric material, or a material which is plated with a biocompatible material. The tube 20 can also be formed of another material suitable for its intended purpose and suitable to the etching process of the type described and claimed herein. In the illustrated embodiment, the tube 20 is a stainless steel cylinder that is cut to a desired length and has a desired wall thickness. The process of forming the tube 20 is well known extrusion technology. It is preferable to have the tube relatively consistent in diameter, concentricity, thickness, and seamless.

Figure 4:
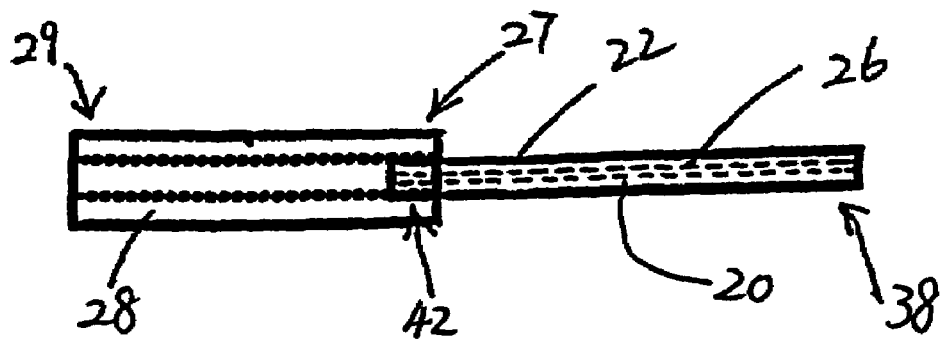
FIG. 4 is a side view of a handle attached to an end of the tube of FIG. 3.

To process the tube 20, the first step is preparation. As indicated in blocks 404 and 406 of FIG. 1, the preparation step includes cleaning and drying the tube 20. It is preferable to clean and remove contaminates on the inner and outer surfaces 26 and 22 of the tube 20. In one particular prototype as shown in FIG. 4, a first end 27 of a tubular handle 28 is attached (e.g., by friction fit) to a second end 42 of the tube 20 with about 0.25 inch overlap, so that the tube 20 can be handled without being touched. Initially, the tube is cleaned in NaOH for about one minute and rinsed. Then, the tube is cleaned in HCl for about one minute and rinsed. The cleaning stage involves immersing the tube 20 in the cleaning solution and removing the tube 20 from the solution several times, so that the solution can reach the inner surface 26 and the outer surface 22 of the tube 20. Optionally, a vacuum can be used to force the cleaning solution to pass through the tube under certain pressure, so that the inner surface 26 of the tube 20 can be thoroughly cleaned. Plasma cleaning can also be used to enhance photosensitive resist adhesion. The approach described above is just an example of handling and cleaning a small volume of tubes. Other approaches for handling and cleaning a large volume of tubes can also be used.

Figure 5:
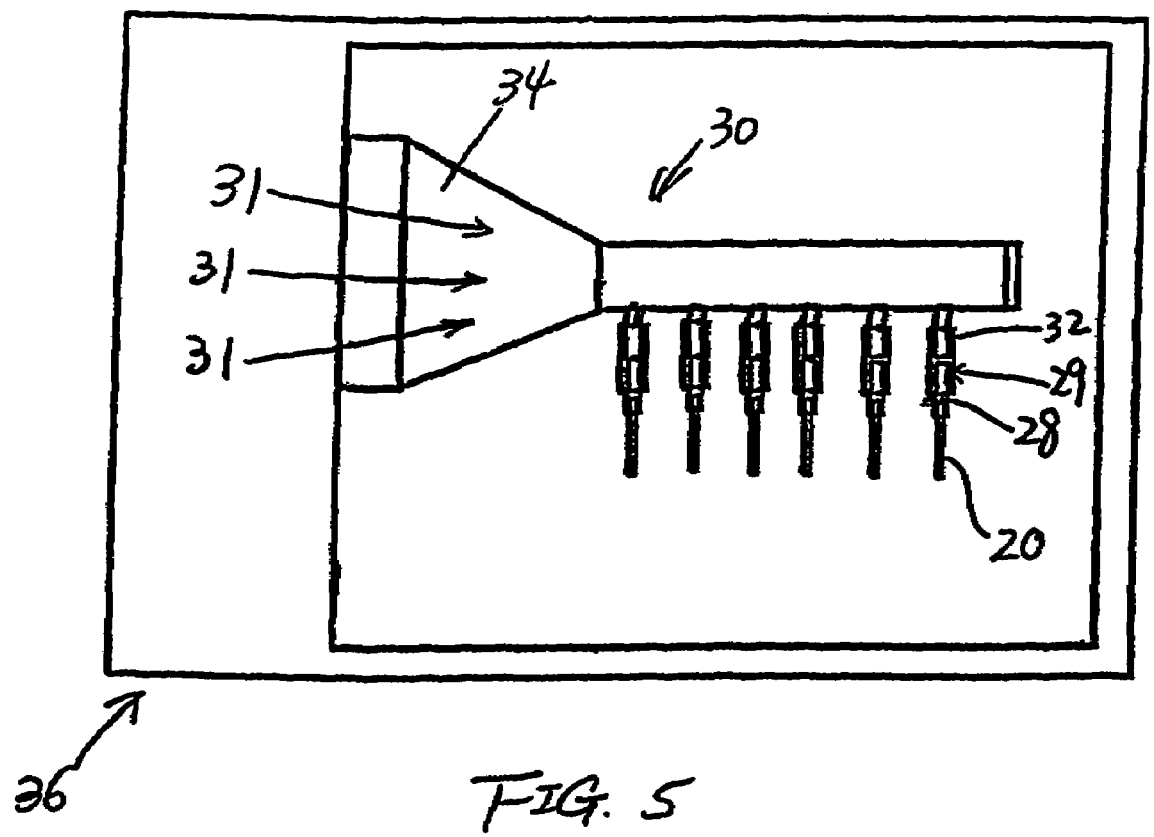
FIG. 5 is a side view of a device used to dry the tube of FIG. 3 with airflow.

After the tube 20 is cleaned (step 404), the next stage is drying the tube 20 (step 406). In an example approach as shown in FIG. 5, a second end 29 of the tubular handle 28 is inserted into a port 32 of a drying device 30 in an oven 36. The funnel 34 of the drying device 30 collects hot air 31 from the oven 36 and forces the air to pass through the port 32, the tubular handles 28, and the tubes 20, respectively. In this approach, the tube 20 is dried in the oven 36 at about 95° C. for about 30 minutes.

After being cleaned and dried, the outer surface 22 of the tube 20 will be coated with negative photosensitive resist as indicated in block 408 of FIG. 1. One characteristic of the negative photosensitive resist is that it is more flexible than positive photosensitive resist when it is dry. The negative photosensitive resist also has the characteristics of high strength and high adhesion when it is dry. The brand of the negative photosensitive resist used for the prototype is Shipley SN50. Because the negative photosensitive resist is more flexible and has the characteristics of high strength and high adhesion when it is dry, it is more robust than positive photosensitive resist when coated on the tube.

Figure 6:
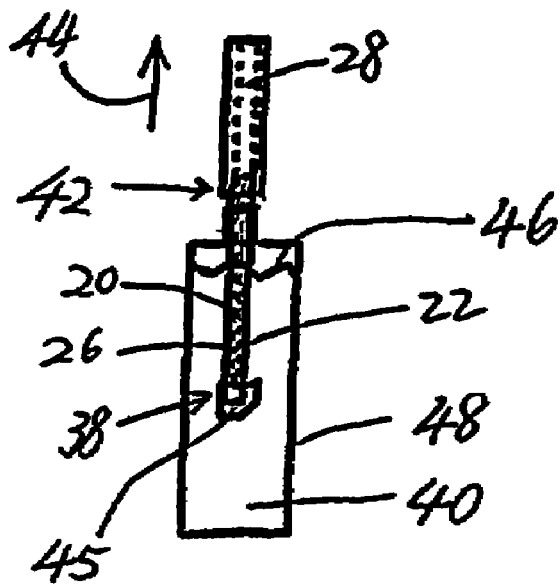
FIG. 6 illustrates coating of the outer surface of the tube of FIG. 3 with negative photosensitive resist.

FIG. 6 illustrates an example approach of coating the outer surface 22 of the tube 20 with the negative photosensitive resist 40. Before coating the outer surface 22 of the tube 20, the opening on a first end 38 of the tube 20 is blocked to be fluid-tight. The opening can be blocked with tape 45 or other materials. A large portion of the tube 20, including the first end 38, but not a second end 42, is then positioned in the negative photosensitive resist 40 in a container 48. The negative photosensitive resist 40 must be kept from reaching the inner surface 26. Then, the tube 20 is withdrawn from the negative photosensitive resist 40 in the direction indicated by arrow 44. The direction of the arrow 44 is generally perpendicular to the surface 46 of the negative photosensitive resist 40. The tube 20 is generally withdrawn at a controlled speed so that the outer surface 22 of the tube 20 can be coated with a uniform thickness. The tube used in this example approach is withdrawn from the negative photosensitive resist 40 at a rate of about 1.25 inches per minute. The rate of withdrawal depends upon many factors, which are specific to the resist. The viscosity of the negative photosensitive resist 40 in this approach is adjusted to provide a coating having a thickness of about 0.0007 inch. The thickness of the coating is preferably about 25% as thick as the annular wall defined by the outer surface 22 and the inner surface 26. The approach described above is just an example of coating a small volume of tubes. Other approaches for coating a large volume of tubes can also be used.

After the tube 20 used in this example approach is withdrawn from the negative photosensitive resist 40, the blocking tape 45 will be removed. As indicated in blocks 410 and 412 of FIG. 1, the next steps are hanging and drying the tube 20. In one prototype of this invention, the tube 20 is hung for about 30 minutes at room temperature to allow some of the solvent on the outer surface 22 to evaporate. After being hung for about 30 minutes, the tube 20 is baked at about 95° C. for about 30 minutes in an oven.

After hanging and drying the tube 20, the next step is exposing the selected pattern portions of the coated outer surface 22 of the tube 20 to a light source as indicated in block 414 of FIG. 1. This step can be done by either transmitting a light source through a patterned photographic film to the coated outer surface 22, or scanning a laser beam on the selected pattern portions of the coated outer surface 22.

Figure 7:
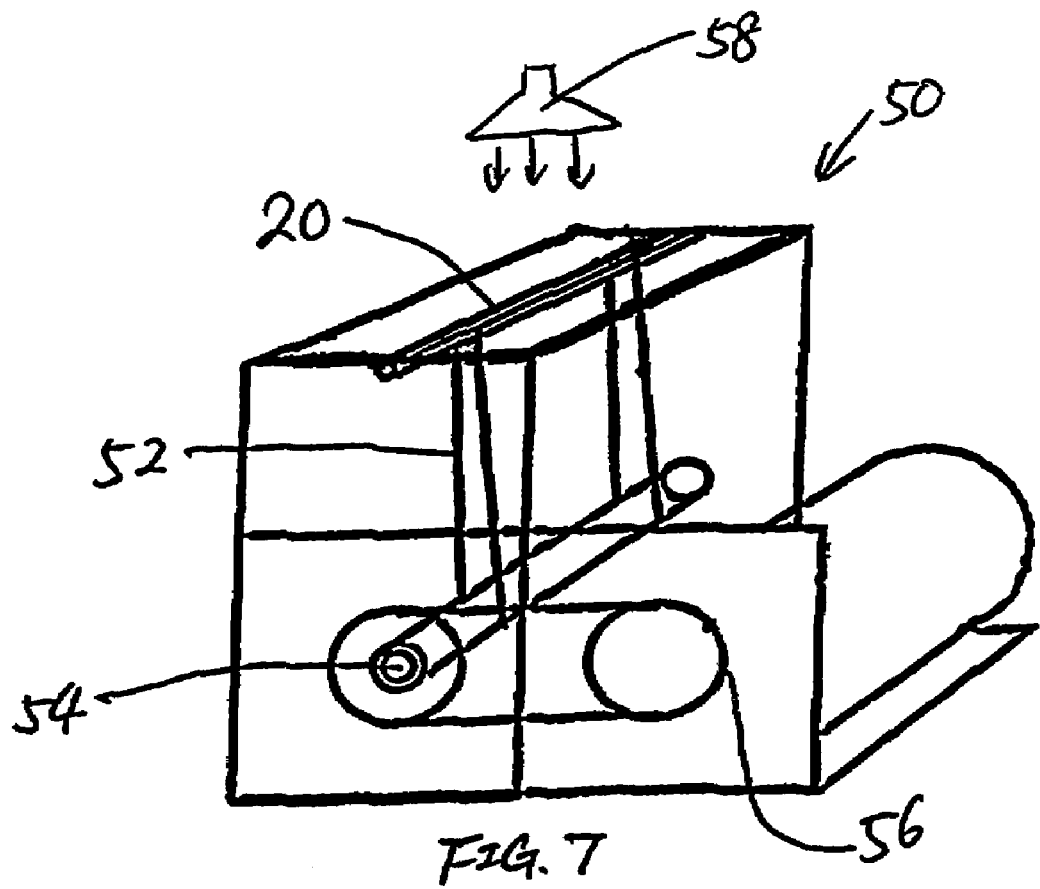
FIG. 7 is a schematic view of a pattern exposing system used to simultaneously rotate the coated tube of FIG. 6, advance a patterned photographic film, and expose the outer surface of the tube to a light source.
Figure 8:
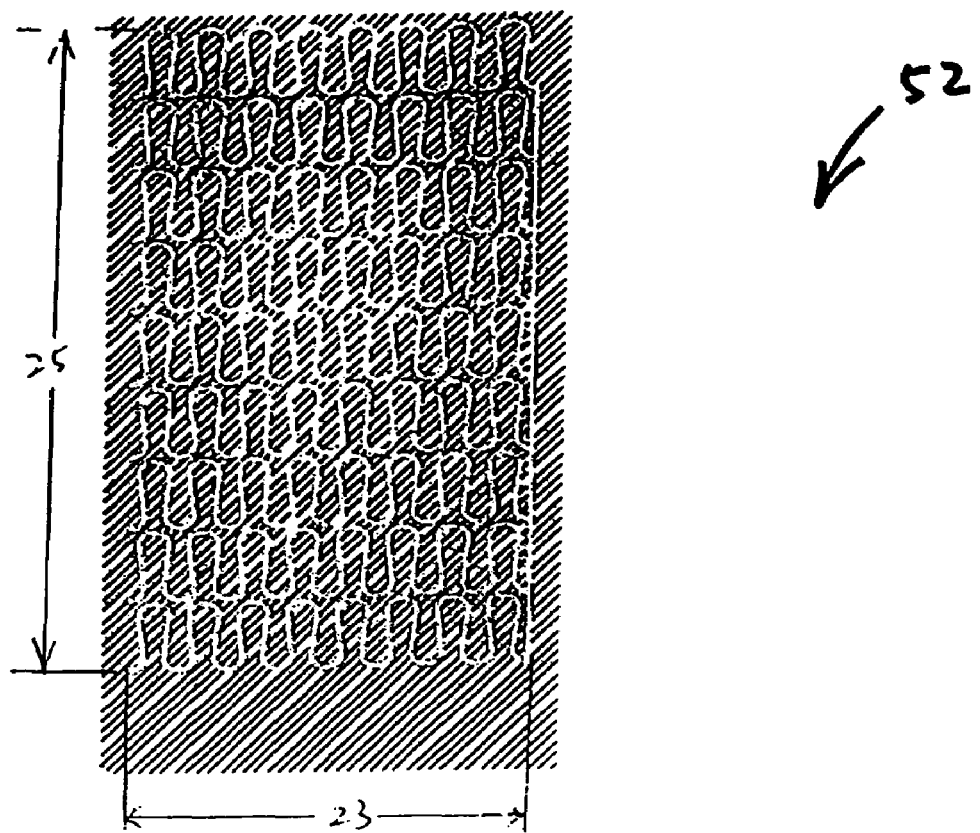
FIG. 8 is a top view of a patterned photographic film shown in FIG. 7.

When transmitting light through a patterned photographic film to the coated outer surface 22 of the tube 20, a pattern exposing system is preferably used. FIG. 7 illustrates a pattern exposing system 50 used to advance a patterned photographic film 52, simultaneously rotate the coated tube 20, and expose the outer surface of the tube 20 to a light source, preferably a UV light source 58. The patterned photographic film 52 as shown in FIG. 8 has a preferred stent configuration imprinted on a transparent photographic film. The drawing of the pattern can be generated on a computer program, then reduced and printed onto a transparent film. The printout is then sent to a film processing facility that reduces the printout and generates a precisely dimensioned negative. The dimensions of the negative must be calibrated to render a specific stent design. The open (transparent) spaces that allow the UV light to pass through the film are represented as solid white lines and alternating loops in FIG. 8. The shaded areas represent the exposed (black) areas of the film that blocks the UV light from passing through the film 20 and exposing the underlying areas to UV. An example of a suitable film that can be employed in the present invention is made from Mylar.

Referring back to FIG. 7, a spool of patterned photographic film 52 is engaged to the tube 20 and a shaft 54 of the system 50. A driven wheel 56 that can be rotated by a motor controls the rotation of the shaft 54 about its longitudinal axis. The rotation of the shaft 54 controls the advancement of the film 52. With the advancement of the film 52, the tube 20 rotates about its longitudinal axis. The movement of the photographic film 52 over the shaft 54 and the tube 20 generates a rotational force that is in unison with the advancement of the film 52. As a result, the outer surface of the tube 20 can be exposed with an equal amount of light. The UV light source 58 is located over the tube 20 and the film 52. With the advancement of the patterned photographic film 52, the tube 20 can be exposed over 360 degrees (i.e., its entire outer surface).

An alternate device (not shown) would be to use a synchronized motor mechanism that would control both the rotation of the shaft and the rotation of the tube. Also not shown is an alternate device that would use a motor to control the rotation of the tube.

Figure 9:
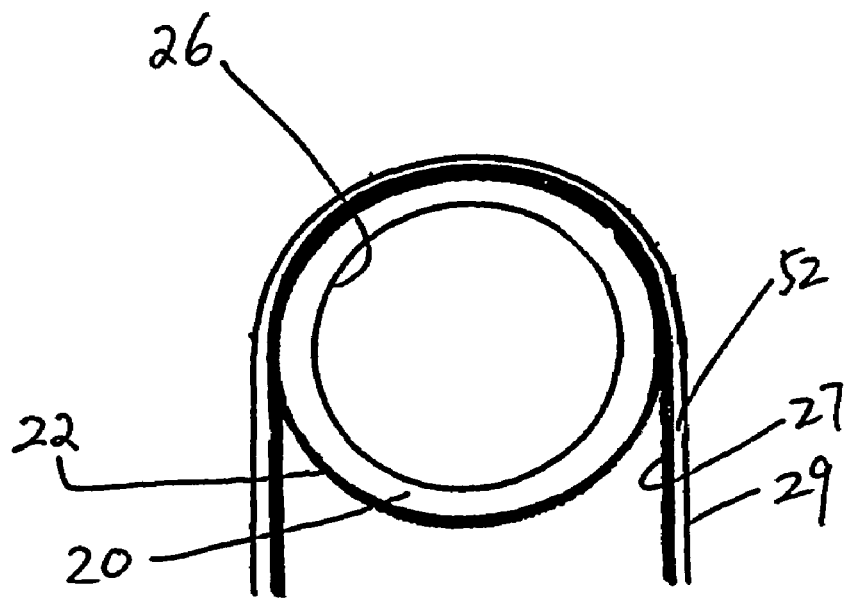
FIG. 9 is a detailed side view of the patterned photographic film of the pattern exposing system shown in FIG. 7 wrapped around a portion of the coated outer surface of the tube.

FIG. 9 is a detailed side view of the patterned photographic film 52 of the pattern exposing system 50 (as shown in FIG. 8) wrapped around a portion of the coated outer surface 22 of the tube 20. The patterned photographic film 52 includes an emulsion side 27 and a non-emulsion side 29. The non-emulsion side 29 preferably faces the UV light source, while the emulsion side 27 preferably faces the coated outer surface 22 of the tube 20. The emulsion material on the emulsion side 27 engages with the coated outer surface 22 of the tube 20 to minimize slippage between the film 52 and the outer surface 22 of the tube 20 during the advancement of the film 52.

Referring to FIGS. 8 and 9, the pattern on the photographic film 52 has a length 25 and a width 23. The length 25 matches the working length of the processed stent. The width 23 matches the circumference of the tube 20 plus double thickness of the resist coated on the tube 20. The width 23 also includes a compensation for shrinkage of the emulsion material on the film 52 (which will be discussed below) as the film 52 wraps around the tube.

The patterns of the photographic film 52 are created on the emulsion material on the emulsion side 27 of the film 52. When the patterned photographic film 52 wraps around a portion of the coated outer surface 22 of the tube 20, the emulsion material on the emulsion side 27 is compressed and the non-emulsion side 29 of the film 52 are stretched. Accordingly, the compensation for shrinkage of the emulsion material on the emulsion side 27 should be included for calculating the width 23 of the film 52.

An alternative way to expose the coated outer surface 22 of the tube 20 is scanning a laser beam on the selected pattern portions of the coated outer surface 22. Laser scanning does not require a patterned photographic film. The wavelength and energy of the laser beam are compatible with the negative photosensitive resist coated on the outer surface 22 of the tube 20. Laser scanning is generally controlled by a motion controller and a computer program.

After the step of exposing the selected pattern portions of the coated outer surface 22, the tube 20 will be developed as indicated in block 416 of FIG. 1. In one prototype of this invention, the tube is developed for about two minutes at room temperature. During the developing step, the portions of the negative photosensitive resist coated on the outer surface that were not exposed to the light are washed away, while the portions of the negative photosensitive on the outer surface that were exposed to the light are retained. Then, the tube 20 will be baked as indicated in block 418 of FIG. 1. In one prototype of this invention, the tube is baked at about 150° C. for about 20 minutes.

The next step as indicated in block 420 of FIG. 1 is coating the inner surface of the tube 20 with positive photosensitive resist. The brand of the positive photosensitive resist used for the prototype is Shipley XP0307. One characteristic of the positive photosensitive resist is that it is more brittle than the negative photosensitive resist and easy to break away when it is dry. The positive photosensitive resist coated on the inner surface of the tube will not be exposed to light. During the step of exposing the outer surface of the tube to an etchant (which will be described below), the etchant is sprayed onto the outer surface of the tube. Because the positive photosensitive resist coated on the inner surface of the tube is relatively brittle when it is dry, the resist on the inner surface breaks away before it starts to peel away from the inner surface after a metal breakthrough. When the positive photosensitive resist coated on the inner surface breaks away, the etchant travels from the outside of the tube, through the channels being etched on the tube, and finally into the inside of the tube. As a result, the etching rate on the inner surface of the tube is generally equal to the etching rate on the outer surface of the tube, so that a straighter perforated wall of the stent can be generated. Since the negative photosensitive resist coated on the outer surface of the tube is relatively flexible and strong when it is dry, it is not used to coat on the inner surface of the tube for single side etching. Conversely, since the positive photosensitive resist coated on the inner surface of the tube is relatively brittle and easy to break away when it is dry, it is not used to coat on the outer surface of the tube for single side etching.

Figure 10:
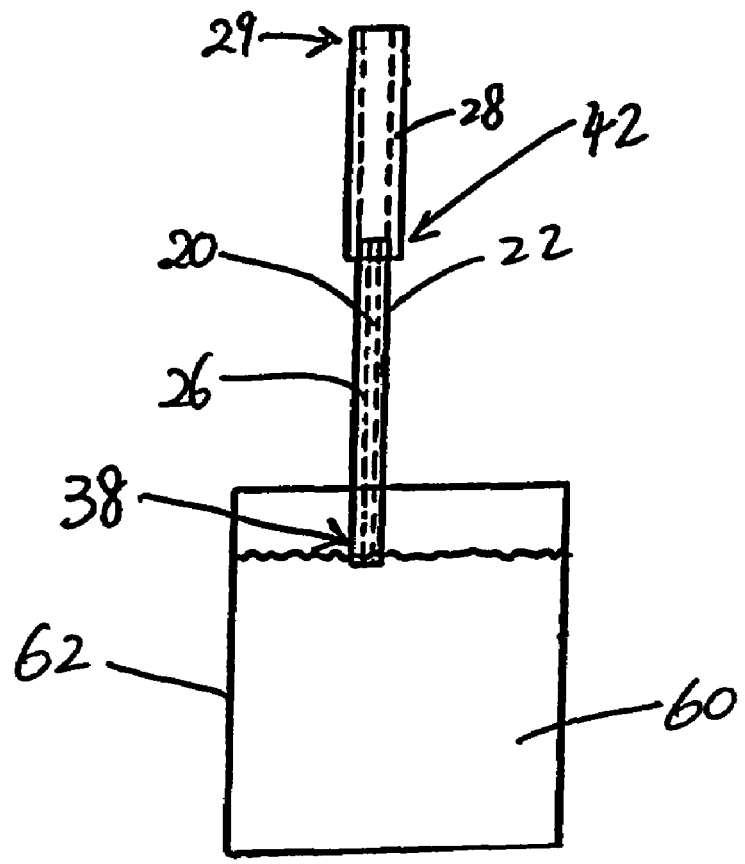
FIG. 10 illustrates coating of the inner surface of the tube of FIG. 3 with positive photosensitive resist.

FIG. 10 illustrates an example approach of coating the inner surface 26 of the tube 20 with the positive photosensitive resist 60. The first end 38 of the tube 20 in this approach is positioned in the positive photosensitive resist 60 in a container 62. The positive photosensitive resist 60 is kept from reaching a large portion of the outer surface 22. A vacuum source (not shown), which can be a syringe or a pump, is attached to the second end 29 of the handle 28. The vacuum source can be operated to draw the positive photosensitive resist 60 into the tube 20, so that the inner surface 26 of the tube 20 can be coated with the positive photosensitive resist 60. The approach described above is just an example of coating a small volume of tubes. Other approaches for coating a large volume of tubes can also be used.

After the inner surface 26 is coated with the positive photosensitive resist 60, the tube will be hung and dried as shown in blocks 422 and 424. In one prototype of this invention, the coated tube will be hung for about 15 minutes at room temperature to allow some of the solvent on the inner surface 26 to evaporate.

The next step as shown in block 424 of FIG. 1 is drying the tube. In one prototype of this invention, the second end 29 of the tubular handle 28 is inserted into the port 32 of the drying device 30 in the oven 36 as shown in FIG. 5. The funnel 34 of the drying device 30 collects hot air 31 from the oven 36 and forces it to pass through the ports 32, the tubular handles 28, and the tubes 20 attached to the tubular handles 28. The tubes 20 are dried in the oven 36 at about 95° C. for about 30 minutes.

Figure 11:
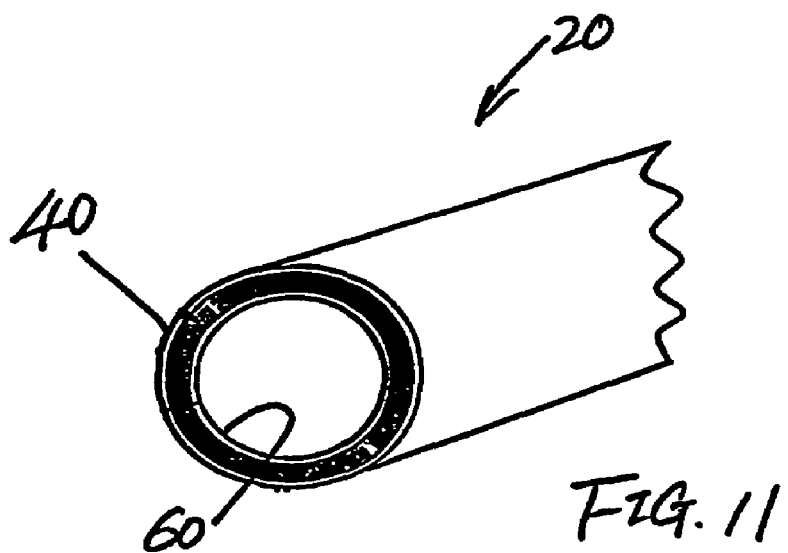
FIG. 11 is a schematic view of a tube having photosensitive resist coated on the inner and outer surfaces.

So far, the outer surface 22 of the tube 20 has been coated with the negative photosensitive resist 40 and imaged. The inner surface 26 has been coated with the positive photosensitive resist 60. The tube 20 that is coated with the negative and positive photosensitive resist 40 and 60 is illustrated in FIG. 11. The next step as indicated in block 426 of FIG. 1 is exposing the outer surface of the tube to an etchant to form a tubular article having a wall structure defined by the selected pattern, such as a radially expandable stent 10 as shown in FIG. 2.

Figure 12:
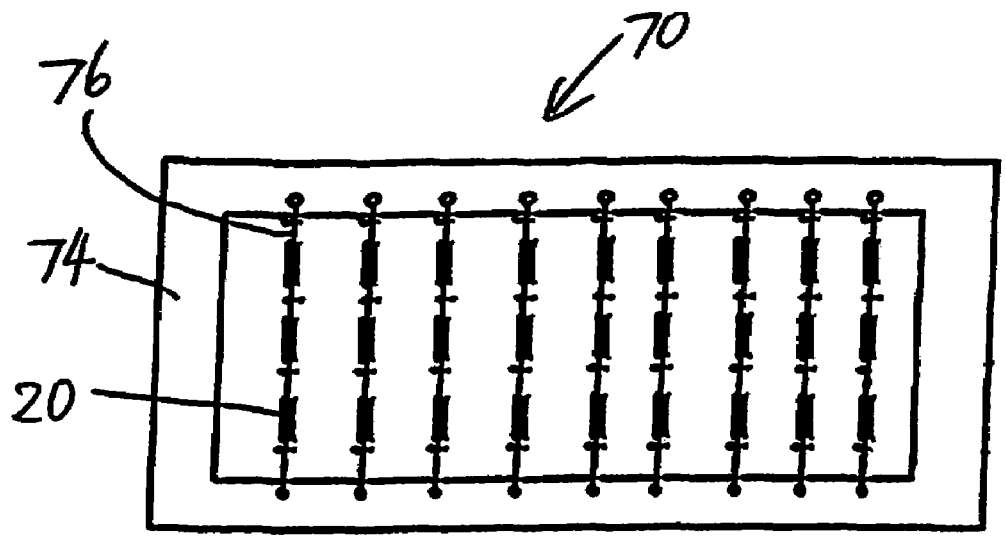
FIG. 12 is a schematic view of a device for exposing an etchant to the outer surface of the tube in accordance with the present invention.

FIG. 12 is a schematic view of a device for exposing an etchant to the outer surface of the tube 20. The device 70 includes a frame 74 and a plurality of strings 76 with two ends attached to the frame 74. The strings 76 are tightly stretched and are generally parallel with each other in the illustrated embodiment. One or more coated tubes 20 are threaded on each of the strings 76. Before threaded on the strings 76, any excess resist on the inner and outer surfaces of the tube 20 is preferably scraped. The etchant is then delivered uniformly to the outer surface of the tubes 20 on the strings 76. During the etching process, the frame 74 is positioned on a conveyer and passes by a number of nozzles that spray the etchant onto both sides of the frame (not shown). Other devices for etching a large volume of tubes can also be used.

Since the portions of the negative photosensitive resist coated on the outer surface that were exposed to the light are retained during the developing step, the immediate underlying portions of the annular wall remain intact during the etching step. Since the portions of the negative photosensitive resist coated on the outer surface that were not exposed to the light are washed away during the developing step, the immediate underlying portions of the annular wall are removed and result in open spaces during the etching step.

After etching, the resist coated on the outer and inner surfaces 22 and 26 of the tube 20 will be removed. This step is indicated in block 428 of FIG. 1. In one prototype of this invention, the negative and positive photosensitive resist left on the tube can be removed with about 50% NaOH or KOH. The tube 20 is immersed in NaOH or KOH at about 40° C. for about five minutes. The negative photosensitive resist (Shipley SN50) used for the prototype can also be removed with Shipley Resist Stripper 448 at about 49° C. for about 45 seconds.

Figure 13:
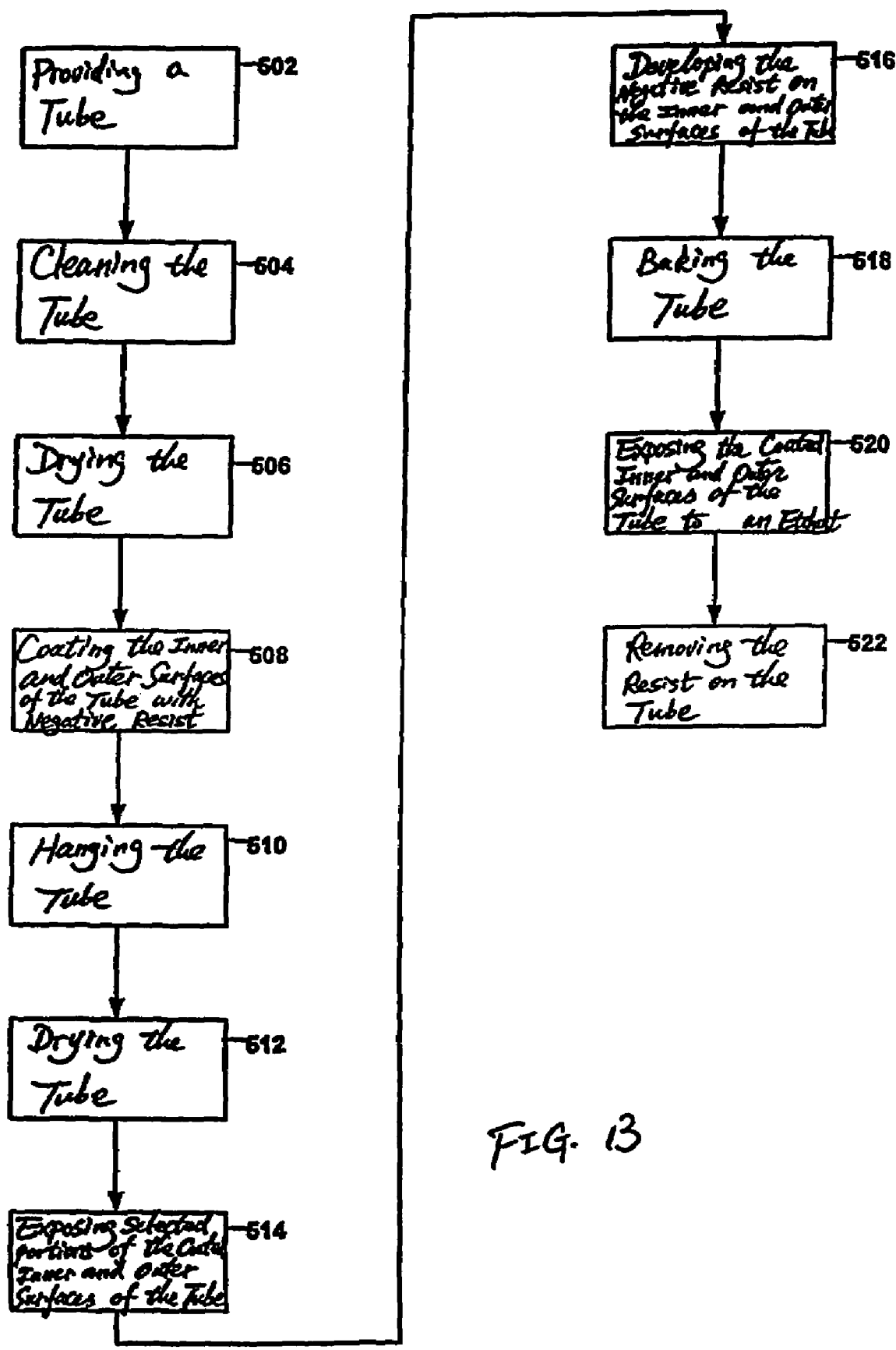
FIG. 13 is a flow chart illustrating the principal steps of the stent fabrication method using double-side etching in accordance with the present invention.

FIG. 13 is a flow chart illustrating the principal steps of a method of fabricating a tubular article having a wall structure defined by a selected pattern, such as a radially expandable stent 10 as shown in FIG. 2, using double-side etching in accordance with the present invention. Steps 502, 504, and 506 of FIG. 13 can be performed in a manner substantially similar to that of steps 402, 404, and 406 of FIG. 1, respectively, as discussed above. In particular, steps 502, 504, and 506 include providing a tube 20 as shown in FIG. 3, as well as cleaning and drying the tube 20. In one particular prototype of the present invention, the tube 20 is attached (e.g., by friction fit) to a tubular handle 28 as shown in FIG. 4, so that the tube 20 can be handled without being touched. This approach is just an example of handling a small volume of tubes. Other approaches for handling a large volume of tubes can also be used.

After being cleaned and dried, the outer and inner surfaces of the tube 20 will be coated with negative photosensitive photo resist as indicated in block 508 of FIG. 13. One characteristic of the negative photosensitive resist is that it is more flexible than positive photosensitive resist when it is dry. The negative photosensitive resist also has the characteristics of high strength and high adhesion when it is dry. The brand of the negative photosensitive resist used for the prototype is Shipley SN50.

Figure 14:
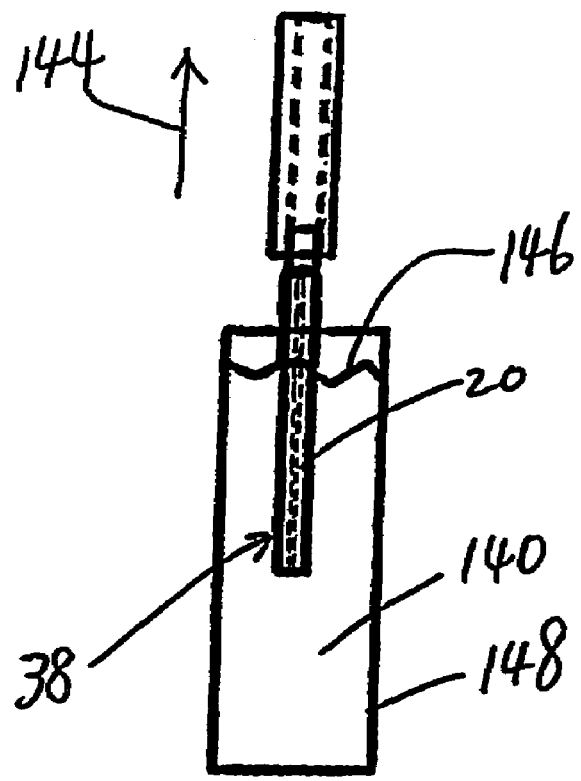
FIG. 14 illustrates coating of the outer and inner surfaces of the tube of FIG. 3 with negative photosensitive resist.

FIG. 14 illustrates an example approach of coating both the outer surface and the inner surface of the tube 20 with negative photosensitive resist 140. The first end 38 of the tube 20 is left open. The entire tube 20 is positioned in the negative photosensitive resist 140 in a container 148. Then, the tube 20 is withdrawn from the negative photosensitive resist 140 in the direction indicated by the arrow 144. The direction of the arrow 144 is generally perpendicular to the surface 146 of the negative photosensitive resist 140. The tube 20 is generally withdrawn at a controlled speed so that both the outer surface and the inner surface of the tube 20 can be coated with a uniform thickness. In this approach, the tube is withdrawn from the negative photosensitive resist 140 at a rate of about 1.25 inches per minute. The rate of withdrawal depends upon many factors, which are specific to the resist. The viscosity of the negative photosensitive resist 140 in this approach is adjusted to provide a coating having a thickness of about 0.0007 inch. The thickness of the coating is preferably about 25% as thick as the annular wall of the tube 20 defined by the outer surface and the inner surface. The approach described above is just an example of coating a small volume of tubes. Other approaches for coating a large volume of tubes can also be used.

When both the inner and outer surfaces of the tube (which will be discussed below) are exposed to an etchant, the resist coated on the inner surface should not break away. Since the positive photosensitive resist is relatively brittle and easy to break away when it is dry, it is not used to coat the inner surface of the tube for double-side etching. The resist coated on the inner and outer surfaces should be flexible and strong to resist the etchant that is supplied to the surfaces. Accordingly, the negative photosensitive resist should be used for double-side etching.

After the tube 20 is withdrawn from the negative photosensitive resist 140, the tube 20 will be hung and dried as shown in blocks 510 and 512. In one prototype of this invention, the tube 20 is hung for about 30 minutes at room temperature to allow some of the solvent on the outer and inner surfaces to evaporate. After being hung for about 30 minutes, the tube 20 is baked at about 95° C. for about 30 minutes in an oven.

After being hung and dried, as indicated in block 514 of FIG. 13, selected pattern portions of the coated outer and inner surfaces of the tube are exposed. This step includes scanning a first laser beam on the selected pattern portions of the coated inner surface and scanning a second laser beam on the selected pattern portions of the coated outer surface. The wavelength and energy of the laser beams are compatible with the negative photosensitive resist coated on the outer and inner surfaces of the tube. Laser scanning is generally controlled by a motion controller and a computer program. The patterns on the inner and outer surfaces of the tube are generally in registration with each other. However, the patterns do not need to be identical. The details of a device for scanning laser beams are discussed below.

After the step of scanning laser beams on the selected pattern portions of the coated outer and inner surfaces, the tube will be developed as indicated in block 516 of FIG. 13. In one prototype of the present invention, the tube is developed for about two minutes at room temperature. During the developing step, the portions of the negative photosensitive resist coated on the outer and inner surfaces that were not exposed to the light are washed away, while the portions of the negative photosensitive on the outer and inner surfaces that were exposed to the light are retained. The tube is then baked as indicated in block 518 of FIG. 13. In one prototype of the present invention, the tube is baked at about 150° C. for about 20 minutes.

As indicated in block 520 of FIG. 13, after the inner and outer surfaces of the tube are coated and imaged, both the outer surface and the inner surface are exposed to an etchant to form a tubular article having a wall structure defined by the selected pattern, such as a radially expandable stent 10 as shown in FIG. 2.

Figure 15:
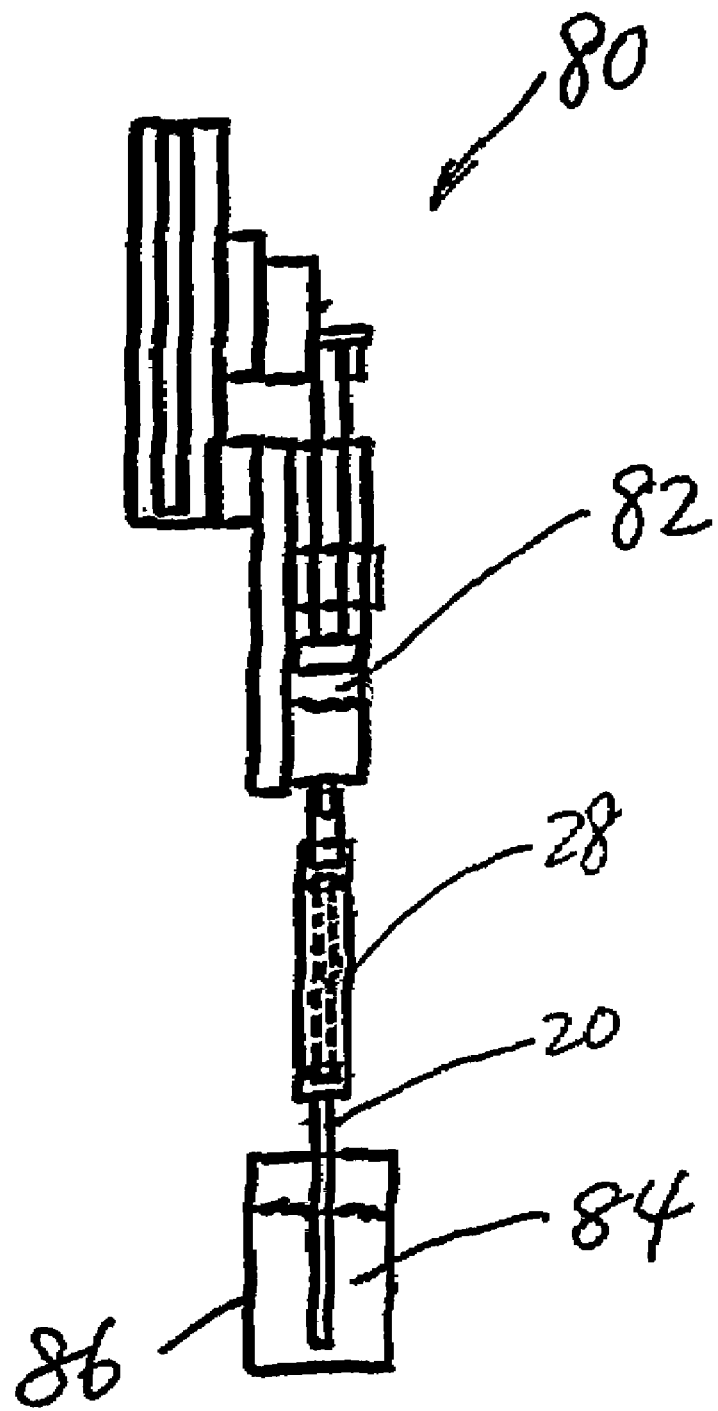
FIG. 15 is a schematic view of a device for exposing the etchant to the outer and inner surfaces of the tube simultaneously in accordance with the present invention.

FIG. 15 is a schematic view of a device for exposing the etchant to the inner and outer surfaces of the tube 20. The tube 20 is positioned in the etchant 84 in a container 86, so that the outer surface is exposed to the etchant 84. The device 80 includes a vacuum source 82 that uniformly delivers the etchant 84 to the inner surface of the tube 20 through the tubular handle 28. The amount of etchant delivered to the inner surface will be controlled approximately equal to the amount of etchant delivered to the outer surface of the tube 20. The device described above is for etching a small volume of tubes. Other devices for etching a large volume of tubes can also be used.

Since the portions of the negative photosensitive resist coated on the outer and inner surfaces that were exposed to the light are retained during the developing step, the immediate underlying portions of the annular wall remain intact during the etching step. Since the portions of the negative photosensitive resist coated on the outer and inner surfaces that were not exposed to the light are washed away during the developing step, the immediate underlying portions of the annular wall are removed and result in open spaces during the etching step.

After etching, the resist coated on the outer and inner surfaces of the tube will be removed. This step is indicated in block 522 of FIG. 13. In one prototype of this invention, the negative photosensitive resist left on the tube can be removed with about 50% NaOH or KOH. The tube is immersed in NaOH or KOH at about 40° C. for about five minutes. The negative photosensitive resist (Shipley SN50) used for the prototype can also be removed with Shipley Resist Stripper 448 at about 49° C. for about 45 seconds.

Figure 16:
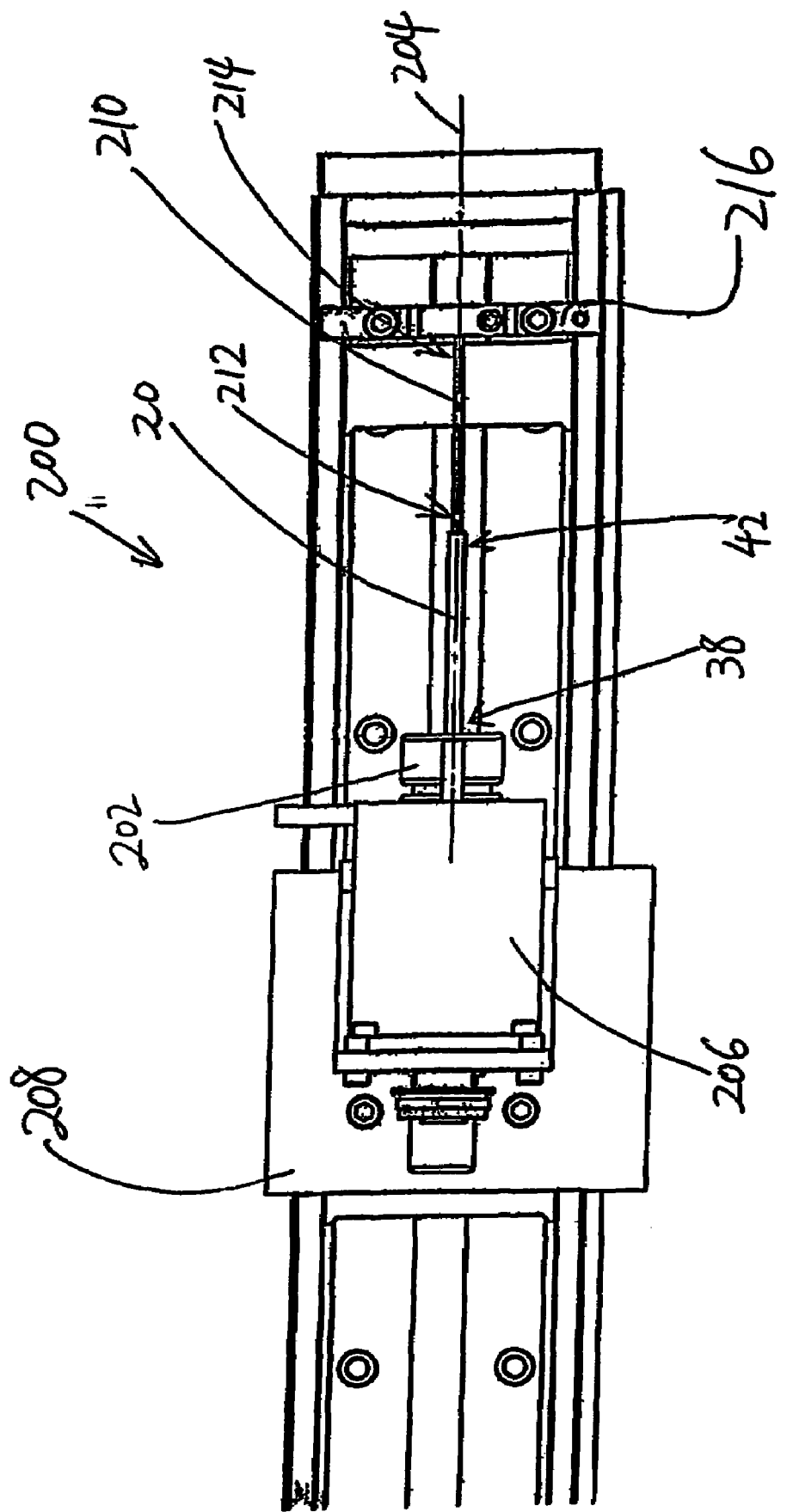
FIG. 16 is a top view of an apparatus for exposing photosensitive resist-coated inner surface of a tube to laser in accordance with the present invention.

As discussed above, the method of fabricating a stent using double-side etching includes exposing the selected pattern portions of the coated outer and inner surfaces of the tube to the first and second laser beam portions, respectively. An apparatus for exposing the negative photosensitive resist-coated inner surface of the tube to laser beams is illustrated in FIG. 16. The apparatus 200 includes a chuck 202 that clamps the first end 38 of the tube 20, on either the inner or outer surfaces of the tube 20, or on both surfaces. The chuck 202 rotates the tube 20 about a predetermined longitudinal axis 204, preferably the longitudinal axis of the tube 20 itself. A rotary drive motor 206 is operatively coupled to the chuck 202 for rotating the tube 20. The apparatus 200 also includes a table 208 for carrying the chuck 202 and the rotary drive motor 206. The table 208 can be controllably moved in a linear direction along the longitudinal axis 204 by a linear drive motor (not shown).

The apparatus 200 further includes an elongated tubular member 210 having a first end 212 and a second end 214. The second end 214 of the elongated tubular member 210 is fixedly mounted on a support 216. Preferably, the support 216 is fixed mounted on the apparatus 200. The elongated tubular member 210 is preferably made of steel.

In an alternative embodiment not shown, the support 216 with the elongated tubular member 210 is controlled by a linear drive motor. The linear drive motor moves the support 216 in a linear direction along the longitudinal axis 204. The table 208 for carrying the chuck 202 and the rotary drive motor 206 is fixedly mounted to the apparatus.

Figure 17:
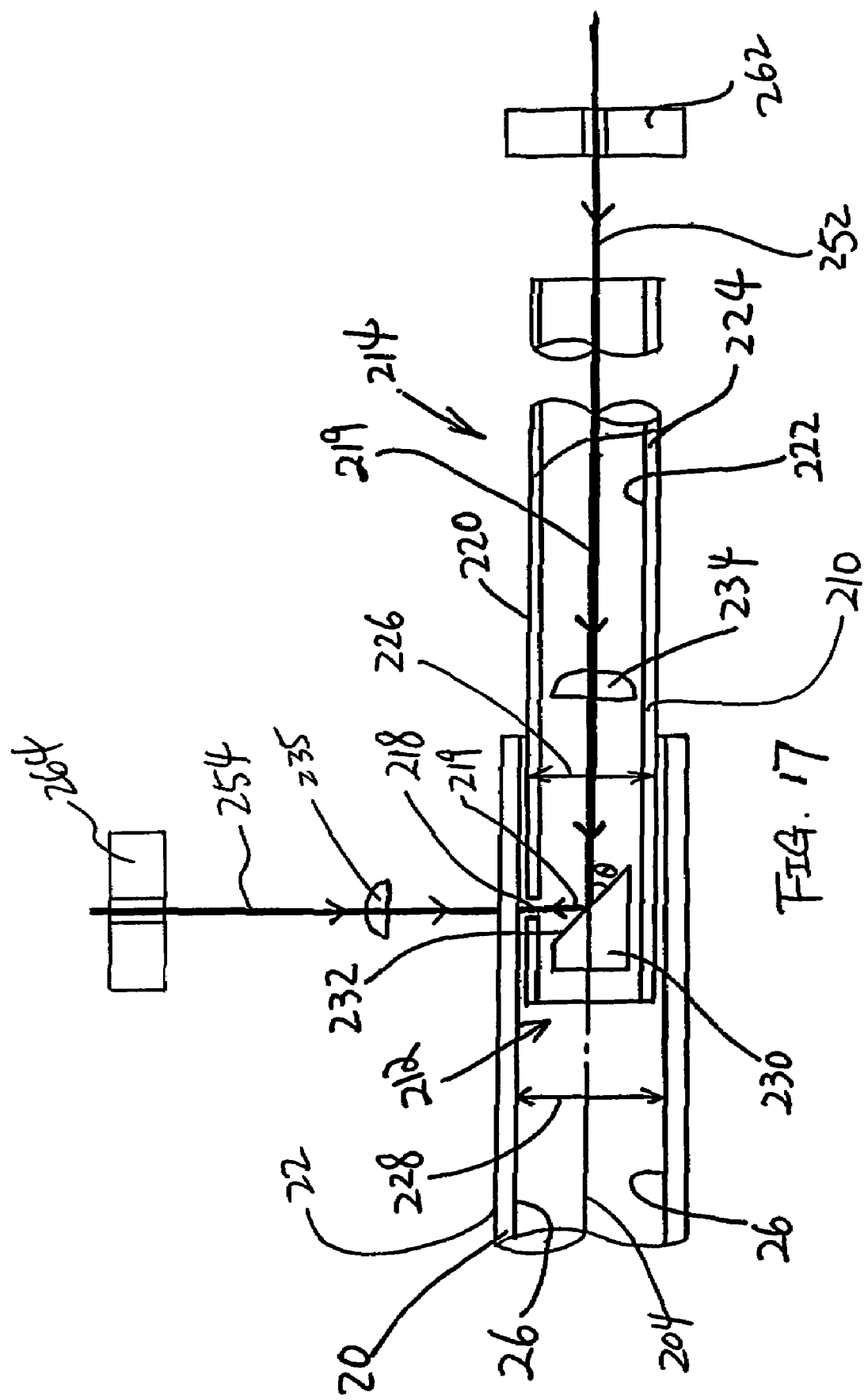
FIG. 17 is a detailed schematic view of a portion of the apparatus shown in FIG. 16.

Referring now to FIG. 17, the elongated tubular member 210 has a longitudinal axis, an exterior surface 220, an interior surface 222, and an annular wall 224 defined by the exterior and interior surfaces 220 and 222. Generally, the longitudinal axis of elongated tubular member 210 is positioned parallel to the longitudinal axis of the tube 20 during operation of the apparatus 200. Preferably, the elongated tubular member 210 and the tube 20 are coaxially positioned. In other words, the elongated tubular member 210 and the tube 20 have a common axis 204 during operation of the apparatus 200. The outside diameter 226 of the elongated tubular member 210 is smaller than the inside diameter 228 of the tube 20, so that the elongated tubular member 210 can be positioned inside the tube 20 without touching the inner surface 26 of the tube 20. Consequently, the tube 20 can be moved relative to the elongated tubular member 210 in a linear direction along the common axis 204 when the elongated tubular member 210 and the tube 20 are coaxially positioned.

The elongated tubular member 210 also includes an aperture 218 extending through the annular wall 224 at the first end 212. A reflective member, such as a mirror 230, is mounted inside the elongated tubular member 210 and adjacent to the aperture 218. The reflecting surface 232 of the mirror 230 and the longitudinal axis 204 forms an angle θ. Preferably, the degree θ is 45 degrees. Further, a lens 234 is preferably positioned in front of the reflecting surface 232 of the mirror 230. The lens 234 is constructed to focus the energy of a laser beam onto the reflecting surface 232.

The apparatus 200 for exposing the negative photosensitive resist-coated inner surface of the tube 20 includes a light source that generates laser. Initially, an incoming laser beam 219 passes the second end 214 of the elongated tubular member 210 and travels to the mirror 230 inside the elongated tubular member 210. The path of the laser beam 219 is generally parallel to the longitudinal axis 204. Preferably, the path of the laser beam 219 and the common axis 204 coincide with each other. When the laser beam 219 reaches the reflecting surface 232 of the mirror 230, the laser beam 219 will change its direction. Preferably, the laser beam 219 becomes perpendicular to the longitudinal axis 204. The position of the mirror 230 can be adjusted to allow the laser beam 219 to pass through the aperture 218 of the elongated tubular member 210. After passing through the aperture 218, the laser beam 219 reaches the negative photosensitive resist-coated inner surface 26 of the tube 20.

Meanwhile, referring back to FIG. 16, the rotary drive motor 206 and the linear drive motor, which are controlled by a computer program, operate the table 208 and the chuck 202, respectively. The table 208 moves the tube 20 in a linear direction along the longitudinal axis 204, while the chuck 202 rotates the tube 20 about the longitudinal axis 204. By controlling both the rotary motion of the chuck 202 and the linear motion of the table 208, almost any conceivable pattern resulting from a combination of rotary and linear displacements may be drawn, i.e., the coating exposed, on the inner surface of the tube 20.

The purpose of the tubular member 210 with the aperture 218 and the reflective member 230 is to direct and control a laser beam onto the inner surface of the tube to finish an imaging process. Other types of elongated devices that are capable of being extended into the tube for transmitting a laser beam to the inner surface of the tube can also be used. The elongated device does not need to be a tubular member and does not need to have an aperture extending through the wall of the tubular member.

The apparatus 200 further includes a mechanism for transmitting a laser beam to the outer surface of the tube 20. Preferably, the apparatus 200 includes a beam splitter adjacent to the light source that generates laser (not shown). The beam splitter is a well known device in industry. The splitter splits the laser beam into two beam portions. The first laser beam portion 252 passes through the elongated tubular member 210 and is directed to the coated inner surface 26 of the tube 20, while the second laser beam portion 254 is directed to the outer surface 22 of the tube 20. A lens 235 is preferably positioned in the route of the second laser beam portion 254. The lens 235 is constructed to focus the energy of the second laser beam portion 254 onto the outer surface 22. It is important that the patterns on the inner and outer surfaces 26 and 22 of the tube 20 are generally in registration with each other. However, the patterns do not need to be identical.

Different patterns on the inner and outer surfaces 26 and 22 of the tube 20 are beneficial for creating partially etched features on the tube 20 during the double-side etching process. The partially etched features on the stent can also be used for storing drugs.

The apparatus 200 further includes a first shutter 262 positioned in the route of the first laser beam portion 252 and a second shutter 264 positioned in the route of the second laser beam portion 254. If the first shutter 262 is shut, only the outer surface 22 of the tube 20 is exposed to the second laser beam portion 254. Conversely, if the second shutter 264 is shut, only the inner surface 26 of the tube 20 is exposed to the first laser beam portion 252. The laser exposing process with the first and second shutters can generate different patterns on the inner and outer surfaces of the tube. The different patterns are beneficial for creating partially etched features on the surfaces of the tube during the double-side etching process. The partially etched features on the stent can be used for storing drugs.

It is important to note that the methods and devices described above are not limited to fabrication of stents. These methods and devices are generally applicable to fabrication of tubular articles having wall structures defined by selected patterns.

All patents and patent applications disclosed herein, including those disclosed in the background of the invention, are hereby incorporated by reference. Although the present invention has been described with reference to preferred embodiments, workers skilled in the art will recognize that changes may be made in form and detail without departing from the spirit and scope of the invention. In addition, the invention is not to be taken as limited to all of the details thereof as modifications and variations thereof may be made without departing from the spirit or scope of the invention.

The invention claimed is:

1. A method for fabricating a tubular article having a wall structure defined by a selected pattern, the method comprising the steps of:
providing a tube having an outer surface and an inner surface;
coating the outer surface of the tube with first photosensitive resist;
exposing the selected pattern portions of the coated outer surface of the tube;
developing the first photosensitive resist coated on the outer surface of the tube;
coating the inner surface of the tube with second photosensitive resist wherein the second photosensitive resist is more brittle than the first photosensitive resist when the first and second photosensitive resist are dry; and
exposing the tube to an etchant to form a tubular article having the wall structure defined by the selected pattern.

2. A method for fabricating a tubular article having a wall structure defined by a selected pattern, the method comprising the steps of:
providing a tube having an outer surface and an inner surface;
coating the outer surface of the tube with negative photosensitive resist;
exposing the selected pattern portions of the coated outer surface of the tube;

developing the negative photosensitive resist coated on the outer surface of the tube;

coating the inner surface of the tube with positive photosensitive resist; and exposing the coated outer surface of the tube to an etchant to form a tubular article having the wall structure defined by the selected pattern.

3. The method of fabricating a tubular article of claim 2, wherein exposing selected pattern portions of the coated outer surface of the tube includes transmitting light to the outer surface of the tube through a patterned photographic film that wraps around at least a portion of the outer surface of the tube.

4. The method of fabricating a tubular article of claim 2, wherein exposing selected pattern portions of the coated outer surface of the tube includes scanning a laser beam on the selected pattern portions of the coated outer surface.

5. The method of fabricating a tubular article of claim 2, wherein coating the inner surface of the tube with positive photosensitive resist includes the steps of:

positioning a first end of the tube into the positive photosensitive resist;

attaching a vacuum source to a second end of the tube; and operating the vacuum source to draw the positive photosensitive resist to the inner surface of the tube.

6. The method of fabricating a tubular article of claim 2, wherein exposing the coated outer surface of the tube to an etchant includes the steps of:

threading the tube on a string; and delivering the etchant to the outer surface of the tube on the string.

7. The method for fabricating a tubular article of claim 2, wherein the positive photosensitive resist is more brittle than the negative photoresist when the positive and negative photoresist are dry.

8. The method for fabricating a tubular article of claim 2, wherein the negative photosensitive resist is more flexible and stronger than the positive photoresist when the positive and negative photoresist are dry.

9. The method for fabricating a tubular article of claim 2, wherein the positive photosensitive resist is relatively brittle and the negative photosensitive resist is relatively flexible and strong when they are dry.

10. The method for fabricating a tubular article of claim 2 including fabricating a radially expandable stent.

11. The method of fabricating a tubular article of claim 2, wherein coating the outer surface of the tube with negative photosensitive resist includes the steps of:

blocking an opening on a first end of the tube to be fluid-tight;

positioning at least a portion of the tube including the first end of the tube, but not a second end of the tube, in the negative photosensitive resist to keep the resist from reaching the inner surface of the tube; and separating the tube from the negative photosensitive resist.

12. The method of fabricating a tubular article of claim 11, wherein the tube is separated at a controlled speed so that the outer surface can be coated with a uniform thickness.

* * * * *